(12) United States Patent
Groene et al.

(10) Patent No.: US 7,122,182 B2
(45) Date of Patent: Oct. 17, 2006

(54) ONCOLYTIC VIRUS THERAPY

(75) Inventors: William S. Groene, New Market, MD (US); Jeffrey A. Miller, Lincoln University, PA (US); Stephen N. Mueller, Myersville, MA (US)

(73) Assignee: Wellstat Biologics Corporation, Gaithersburg, MD (US)

( * ) Notice: Subject to any disclaimer, the term of this patent is extended or adjusted under 35 U.S.C. 154(b) by 512 days.

(21) Appl. No.: 10/142,405

(22) Filed: May 9, 2002

(65) Prior Publication Data

US 2003/0077819 A1 Apr. 24, 2003

Related U.S. Application Data

(60) Provisional application No. 60/290,051, filed on May 11, 2001.

(51) Int. Cl.
*A61K 35/14* (2006.01)
*A61K 35/76* (2006.01)

(52) U.S. Cl. .................. 424/93.6; 424/93.71; 424/93.72
(58) Field of Classification Search .............. 424/93.71, 424/93.72, 93.6
See application file for complete search history.

(56) References Cited

U.S. PATENT DOCUMENTS

| 5,126,132 A | 6/1992 | Rosenberg |
| 6,207,147 B1 | 3/2001 | Hiserodt et al. |
| 6,428,968 B1 | 8/2002 | Molnar-Kimber et al. |

FOREIGN PATENT DOCUMENTS

| WO | WO 94/25627 | * 11/1994 |
| WO | WO 99/18799 | 4/1999 |
| WO | WO 99/29343 | * 6/1999 |
| WO | WO 00/62735 | 10/2000 |
| WO | WO 01/19380 | 3/2001 |

OTHER PUBLICATIONS

Perkins, In: Basic and Clinical Immunology, Fudenberg et al, Ed., 1978, pp. 177–182.*
Termeer et al, Cancer Gene Therapy, 2000, vol. 7, pp. 316–323.*
Harfast et al (Journal of Immunology, 1977, vol. 118, pp. 1132–1137).*
Schirrmacher et al (Clinical Cancer Research, 1997, vol. 3, pp. 1135–1148).*
Dong et al, In: Vaccine Design: The Subunit and Adjuvant Approach, Powell et al, Ed.s, 1995, pp. 625–643.*
Bohlen et al, (Blood, 1993, Volt, 82, pp. 1803–1812).*
Bonina, et al., "Human Mononuclear Phagocytic Cell Interaction with some Paramyxoviridae", Giom. Batt. Virol. Immun., LXXVIII, pp. 254–261, 1985.
Faden, et al., "The In Vitro Effect of Newcastle Disease Virus on the Metabolic and Antibacterial Functions of Human Neutrophils", Blood, vol. 58, No. 2, pp. 221–227, Aug. 1981.
Schimmacher, et al., "Newcastle Disease Virus activates macrophages for anti–tumor activity", International Journal of Oncology, vol. 16, pp. 363–373, 2000.
Baranowski, et al., "Evolution of Cell Recognition by Viruses", Science, vol. 292, pp. 1102–1105, May 2001.
Pecora, et al., "Phase I Trial of Intravenous Administration of PV701, an Oncolytic Virus, in Patients with Advanced Solid Cancers", Journal of Clinical Oncology, vol. 20, No. 9, pp. 2251–2266, May 2002. (esp. last para. on p. 2253, first para. on p. 2254, and first full para. on p. 2262).
"An Intravenous Phase I Trial of Replication–Competent Virus, PV701, in the Treatment of Patients with Advanced Solid Cancers (Abstract #1009)–Dr. Andrew Pecora—Presented May 13, 2001, ImmunoBiology Session American Society of Clinical Oncology—Palace Hotel, San Francisco, California", transcript pp. 1–10, (esp. first full para. on p. 7 and p. 9).
An Intravenous Phase I Trial of a Replication–Competent Virus, PV701, in the Treatment of Patients with Advanced Solid Cancers slide presentation, May 13, 2001.
Howe, et al., "Virus–Erythrocyte Interactions", Advances in Virus–Research, vol. 17, pp. 1–50, 1972.
Woodruff, et al., "Virus–Induced Alterations of Lymphoid Tissues II. Lymphocyte Receptors for the Newcastle Disease Virus", Cellular Immunology, vol. 5, pp. 296–306, 1972.
Woodruff, et al., "Lymphocyte Receptors for Myxoviruses and Paramyxoviruses", The Journal of Immunology, vol. 112, No. 6, pp. 2176–2183, Jun. 1974.

* cited by examiner

*Primary Examiner*—Karen A. Canella
(74) *Attorney, Agent, or Firm*—Lewis J. Kreisler

(57) ABSTRACT

A method of treating a human subject with cancer is disclosed. A pharmaceutical composition is administered to the subject, the pharmaceutical composition comprising human leukocytes and a replication-competent oncolytic virus in suspension in a physiologically acceptable solution. Alternatively the pharmaceutical composition comprises human leukocytes or platelets infected with an oncolytic virus.

15 Claims, No Drawings

ONCOLYTIC VIRUS THERAPY

This application claims the benefit of U.S. Provisional Application No. 60/290,051, filed May 11, 2001, the content of which is incorporated herein by reference.

BACKGROUND OF THE INVENTION

"Treatment of Neoplasms with Viruses" (WO 00/62735) relates to a method of administering viruses that are able to replicate and kill neoplastic cells with a deficiency in the IFN-mediated antiviral response. One specific aspect of this patent involves the "systemic" administration of such viruses.

Paramyxoviruses are known to interact with erythrocytes and agglutinate them. They are reported to elute from erythrocytes with lower efficiency than influenza viruses. Howe, C. and Lee, L. T. (Adv. Virus Res. 17:1–50, 1972). Furthermore, the specific inhibition of hemagglutination of erythrocytes caused by paramyxoviruses through neutralization by antibodies specific to viral coat proteins is a well understood phenomenon.

Schirrmacher et al (Int. J of Oncology 16:363–373, 2000) have shown that NDV will activate mouse macrophages for anti-tumor activity. The experimental results appearing below demonstrate that NDV does not preferentially bind to mouse leukocytes when added to mouse whole blood.

Bonina et al (Giorn. Batt. Virol. Immun., LXXVIII, 254–261, 1985) show that human macrophages could support the growth of NDV.

Woodruff et al (Cellular Immunology 5:296–306, 1972) and Woodruff and Woodruff (J of Immunology 112 (6);2176–2183, 1974) found that NDV agglutinates rat, mouse and human lymphocytes in vitro.

Faden et al (Blood, 58:221–7,1981) showed that NDV will bind to human neutrophils in vitro.

None of the above indicate any preferential binding of NDV to leukocytes over erythrocytes.

The literature describes the binding of NDV to red blood cells (usually chicken). As NDV is not pathogenic in man it is a surprising result to find that NDV binds preferentially to the white blood cell component of human blood.

The literature indicates that the binding of NDV to cells occurs through the interaction of the Neuraminidase of the viral HN protein with sialic acid residues attached to cell surface proteins. Human erythrocytes have a very high density of sialic acid residues attached to surface proteins. The ratio of erythrocytes to leukocytes in human blood is approximately 1000 to 1. Thus, it is especially surprising that NDV binds to the leukocyte fraction instead of the much more numerous erythrocytes.

SUMMARY OF THE INVENTION

This invention provides a method of treating a human subject with cancer, comprising administering to the subject an amount of a pharmaceutical composition effective to treat the subject, the pharmaceutical composition comprising human leukocytes and a replication-competent oncolytic virus in suspension in a physiologically acceptable solution, wherein the virus binds specifically to the leukocytes; and the ratio of plaque-forming units of the virus to number of leukocytes in the composition is at least 1:100, thereby treating the subject.

This invention provides a method of treating a human subject with cancer, comprising administering to the subject an amount of a pharmaceutical composition effective to treat the subject, the pharmaceutical composition comprising human cells infected with an oncolytic virus in suspension in a physiologically acceptable solution, wherein the cells are leukocytes or platelets, thereby treating the subject.

This invention provides the use of a pharmaceutical composition to treat a human subject with cancer or in the manufacture of a medicament for the treatment of cancer, the pharmaceutical composition comprising: (a) human leukocytes and a replication-competent oncolytic virus in suspension in a physiologically acceptable solution, wherein the virus binds specifically to the leukocytes and the ratio of plaque forming units of the virus to number of leukocytes in the composition is at least 1:100; or (b) human cells infected with an oncolytic virus in suspension in a physiologically acceptable solution, wherein the cells are leukocytes or platelets. Uses (a) and (b) are linked in that practicing use (a) generally involves practicing use (b) since the replication-competent oncolytic virus will generally infect the leukocytes.

This invention is based, in part, on the finding that an oncolytic virus such as NDV binds to leukocytes and platelets. NDV binds leukocytes preferentially compared to erythrocytes. Tumors involve inflammatory processes. Therefore leukocytes to which an oncolytic virus is bound or which are infected with an oncolytic virus are a particularly effective means of delivering oncolytic viruses.

DETAILED DESCRIPTION OF THE INVENTION

As used herein the term "human cells" means cells isolated from a human, or cultured cells that have been derived from cells isolated from a human and/or whose nucleic acid component has been altered by, for example, immortalization, irradiation or recombinant means. "Human leukocytes" and "human platelets" are human cells that are leukocytes and platelets, respectively. Except where otherwise specified or required by the context the terms "cells" or "human cells" refer to leukocytes and/or platelets.

As used herein the term "plaque-forming unit" (pfu) means one infectious virus particle.

As used herein the term "multiplicity of infection" (MOI) means the number of infectious virus particles added per cell.

As used herein the term "clonal virus" means a virus derived from a single infectious virus particle and for which individual molecular clones have significant nucleic acid sequence homology. For example, the sequence homology is such that at least eight individual molecular clones from the population of virions have a sequence homology greater than 95% over 300 contiguous nucleotides.

As used herein the term "leukocyte virus complex" (LVC) means the complex formed when an oncolytic virus is mixed with a leukocyte cell population and the virus has become associated with the cells. The term includes both cells where the virus is bound to the outside of the cell and cells which are infected by the virus.

As used herein a virus is said to "bind(s) specifically" to a given cell if such virus binds to such cell with a greater specificity than such virus binds to erythrocytes. The terms bind(s) specifically and specifically bind(s) are used interchangeably.

As used herein "NDV" is an abbreviation for Newcastle Disease Virus.

As used herein the term "replication-competent" virus refers to a virus that produces infectious progeny in cancer cells.

As used herein the transitional term "comprising" is open-ended. A claim utilizing this term can contain elements in addition to those recited in such claim.

In accordance with this invention the human cells can be derived from any source. They can be donated by someone other than the subject. However if feasible it is generally preferred to use cells donated by the subject, for safety reasons. Optionally cells isolated from the donor can first be grown in culture and the cultured cells are also considered to be cells of the donor from which they were derived. Examples of cultured cells that can be utilized in accordance with this invention include immortalized human leukocyte cell lines. Suitable cell lines are publicly available from sources such as the American Type Culture Collection, for example U-937 (ATCC No. CRL-1593.2) and KG-1 (ATCC No. CCL-246).

The leukocytes utilized in accordance with this invention (e.g. monocytes, neutrophils and lymphocytes including tumor-infiltrating lymphocytes) can be active or inactive. Techniques for inactivating leukocytes include irradiation.

The cells utilized in accordance with this invention can be isolated (for example by leukopheresis in the case of leukocytes). However it is not necessary to isolate the cells and whole blood can be used instead, in which case the pharmaceutical composition comprises the oncolytic virus suspended in whole blood or whole blood containing leukocytes and/or platelets infected with the virus. Optionally the leukocytes or platelets are first isolated from whole blood, mixed or infected with the virus and then added back to the other blood components.

In different embodiments of this invention the leukocytes are selected from monocytes, neutrophils and lymphocytes. In a more specific embodiment of this invention the leukocytes are tumor-infiltrating lymphocytes (TILs). TILs may be prepared for example by the method described in Rabinowich, H., et al., (Cancer Res. 47: 173–7, 1987).

In accordance with this invention the oncolytic virus utilized can be of low (lentogenic), moderate (mesogenic) or high (velogenic) virulence. The level of virulence is determined in accordance with the Mean Death Time in Eggs (MDT) test. (Alexander, "Chapter 27: Newcastle Disease" in Laboratory Manual for the Isolation and Identification of Avian Pathogens, $3^{rd}$ ed., Purchase, et al. eds. (Kendall/Hunt, Iowa), page 117.) Viruses are classified by the MDT test as lentogenic (MDT>90 hours); mesogenic (MDT from 60–90 hours); and velogenic (MDT<60 hours).

In an embodiment of this invention the virus is a clonal virus.

Referring to the method or use in which the pharmaceutical composition utilized comprises leukocytes and oncolytic virus in suspension, in an embodiment of such method the ratio of plaque-forming units of the virus to number of leukocytes in the composition is at least 1:1. Generally it is preferred that the leukocytes be saturated with active virus particles. In the case of NDV saturation is achieved at a 200:1 ratio of plaque-forming units of the virus to number of leukocytes. Accordingly in an embodiment of this invention the virus is NDV and the ratio of plaque-forming units of the virus to number of leukocytes in the composition is from about 1:1 to about 200:1, and preferably is about 200:1.

In the method or use described above in which the pharmaceutical composition utilized comprises cells infected with an oncolytic virus, in an embodiment of such method the infected cells are at least one-tenth of one percent (0.1%) of the total number of leukocytes and platelets in the composition, more preferably at least thirty percent and most preferably about one hundred percent. The virus utilized can be replication incompetent although preferably it is replication competent.

In an embodiment of this invention the oncolytic virus is selected from the group consisting of a Newcastle Disease Virus (NDV), a Mumps Virus, a Measles Virus, a Vesicular Stomatitis Virus, a Para-influenza Virus, an Influenza Virus, an Adenovirus, a Herpes I Virus, a Vaccinia Virus, and a Reovirus. In a more specific embodiment a Newcastle Disease Virus strain of moderate virulence can be utilized.

The skilled clinician can determine the optimal amount of the composition to be administered in each case. Typically when the cells are leukocytes the effective amount is a daily dosage of the composition containing from $6 \times 10^6$ to $6 \times 10^{10}$ leukocytes per square meter of patient surface area, for example about $6 \times 10^7$ leukocytes per square meter of patient surface area. When the cells are platelets the effective amount is typically a daily dosage of the composition containing from $10^9$ to $10^{11}$ platelets per square meter of patient surface area, for example about $10^{11}$ platelets per square meter of patient surface area.

The daily dosage of the composition can be administered to the subject in multiple administrations in the course of a single twenty-four hour period in which a portion of the daily dosage is administered at each administration. More preferably the daily dosage is administered in a single administration. In an embodiment of this invention the daily dosage of the composition is administered to the subject at a frequency of from one to seven times (i.e. on each of from one to seven days) in a one-week period.

In accordance with this invention, any conventional route of administration is suitable for administering the pharmaceutical composition. For example the composition can be administered intravenously, intratumorally, intraperitoneally or intravesicularly (kidneys). In the case of intravenous administration it is convenient if the volume of the composition administered is from twenty-five milliliters to one liter. In the case of intratumoral administration it is convenient if the volume of composition administered is from one hundred microliters to ten milliliters per tumor mass. In the case of intraperitoneal administration it is convenient if the volume of composition administered is up to two liters. In the case of intravesicular administration it is convenient if the volume of composition administered is up to seventy-five milliliters, preferably from fifty to sixty milliliters. Depending on the amount of pfus of virus and cells to be administered the concentration of the composition can be varied to achieve the desired volume. When the cancer is a solid tumor the composition can be administered by any of the routes given above, for example intravenously or intratumorally. When the cancer is other than a solid tumor (e.g. leukemia) the composition is not administered intratumorally and instead can be administered by the other routes given above, for example intravenously.

The invention will be better understood by reference to the following examples which illustrate but do not limit the invention described herein. In the following examples the NDV used was a triple-plaque purified attenuated (moderately virulent) version of the MK107 strain of Newcastle Disease Virus, described more fully in international patent publication WO 00/62735, published Oct. 26, 2000 (Pro-Virus, Inc.).

EXAMPLES

Example 1

Binding of NDV to Human Blood Cells

Purpose: Investigate the binding of NDV to human blood cells in order to determine which cell types bind the virus.

Materials: Reference lot RL-004 NDV; Antibody Mab2F12 (3.5 mg/ml) is raised to NDV HN protein; BD PharMingen Stain Buffer (PSB) containing 2% fetal bovine serum and 0.02% sodium azide, catalog #554656, lot M059394; Rockland goat anti-mouse polyclonal antibody—phycoerythrin conjugate, catalog #710-1832, lot 7367; Becton Dickinson Immunocytometry Systems 10×FACS Lysing Solution, Cat349202, lot#82026

Method: Human whole blood was collected in citrate tubes (3.2%, 0.105 M, Becton Dickinson #366415). Approximately 4 ml from each of 2 tubes was pooled and kept at room temperature until use. Cells were counted using the trypan blue exclusion method and a hemocytometer. NDV lot number RL-004 (1.3E+10 PFU/ml) was used to infect the cells at MOIs (Multiplicity of Infection, expressed as PFU/cell) of 0.2, 0.05 and 0.02 (along with a negative control of no added virus). After virus was added, tubes were incubated at 37° C. for 30 minutes. Gentle mixing of the tubes to keep cells in suspension was performed at 3 intervals during the incubation period.

The samples were washed twice by adding 2 ml of cold PSB, centrifuging for 5 minutes, 4° C., 2000 rpm, and aspirating the solution away from the cell pellet. The PSB was removed each time by aspiration. The volumes of each sample were adjusted to 1 ml by adding cold PSB. The monoclonal antibody Mab2F12 was added to each sample by adding 20 ul of a solution containing 9.1 μg of the antibody. The samples were incubated for 30 minutes on ice and washed twice again as previously described. The goat anti-mouse—PE reporter antibody was added to each sample by adding 1 ml of a 12 μg/ml solution of this antibody. The samples were again incubated for 30 minutes on ice and washed as described above. For analysis of the leukocyte fraction, 100 μl of each sample was incubated with 3 ml of 1×FACS Lysing Solution for 6 minutes at room temperature. The samples were centrifuged and aspirated as before. The cell pellets were re-suspended in 0.5 ml of PSB. For erythrocyte analysis, 1.5 μl of each sample was added to 2.0 ml of PSB. Samples analysis was performed with a Becton Dickinson FACSCalibur flow cytometer. Forward and side scatter parameters employed linear settings and FL2 detection of phycoerythrin employed logarithmic settings.

Results: The results of the experiment shown in Table 1 indicate that NDV binds preferentially to the leukocyte fraction of human whole blood. At an MOI of 0.05 (to whole blood), 46% of the leukocytes are positive for NDV compared to 0% of the erythrocytes. At an MOT of 0.2 NDV is present on 89% of the leukocytes while bound to only 15% of the erythrocytes. Note that MOI's of 0.05 and 0.2 are approximately 50 and 200 to the leukocytes if the presence of the erythrocytes is discounted. The small amount of NDV binding to erythrocytes at the higher MOI may reflect low affinity binding to sialic residues on proteins present on the surface of these cells.

TABLE 1

| | % Cells Positive for NDV Binding | |
|---|---|---|
| MOI | Erythrocytes | Leukocytes |
| 0.05 | 0 | 46 |
| 0.2 | 15 | 89 |

It is generally appreciated that Paramyxoviridae interact with erythrocytes and produce haemagglutination of the erythrocytes (see How, C. and Lee, L. T., "Virus-Erythrocyte Interactions"). Thus, it is commonly believed that the major cell type involved in the binding of these viruses, including NDV, are the erythrocytes. The binding of NDV to cells is thought to occur through the interaction of the Neuraminidase activity of the viral HN protein to sialic acid residues attached to cell surface proteins. Human erythrocytes have a very high density of sialic acid residues attached to surface proteins for the purpose of keeping the cells in solution in the blood. As the ratio of erythrocytes to leukocytes in human blood is approximately 1000 to 1, it is especially surprising that NDV binds to the leukocyte fraction instead of the vastly more numerous erythrocytes.

Example 2

NDV Associates with Leukocytes in the Presence of NDV Neutralizing Antibody

Introduction/Background: The purpose of this experiment was to assess the ability of NDV to bind to leukocytes in the presence or absence of NDV neutralizing antibody. Human clinical patient 521 received approximately 27 treatment courses of NDV therapy prior to having whole blood drawn for this experiment. Patient 521 displayed significant levels of NDV neutralizing antibodies as detected by plaque neutralization and micro-neutralization assays.

Methods: Human whole blood from a naive donor and patient 521 were collected in citrate tubes (3.2%, 0.105M, Becton Dickenson #366415). The tubes from each donor were kept at room temperature. Whole blood was divided into aliquots and spiked with NDV (lot number RL-005). NDV was spiked at MOIs (multiplicity of infection, expressed as PFU/cell) of 0.2, 0.02 and 0.002 (along with a negative control of no added virus). After virus was added, tubes were incubated at room temperature for 30 minutes. Plasma and leukocytes were isolated from the spiked samples by gradient centrifugation using polymorphprep (Nycomed, Inc.). Plasma was carefully removed from the top of the gradient. Two Leukocyte bands (a polymorphonuclear cell band and a mononuclear cell band) were collected and placed in 0.5×DMEM. Cells were pelleted and resuspended in full strength DMEM. Cells were washed several times to remove the separation media. Leukocytes in each aliquot were enumerated using a Coulter Counter. Known numbers of leukocytes or volumes of plasma were co-cultured or inoculated onto monolayers of HT1080 human fibrosarcoma cells (ATCC, CCL-121) in 25 $cm^2$ tissue culture flasks (Corning). HT1080 cells are highly sensitive to cytolysis by NDV. Monolayers were evaluated qualitatively over several days for the presence of CPE (cytopathic effect). Flasks which exhibited CPE were considered positive.

Results: As shown in Table 2, for both the naive donor and patient 521, at 300,000 leukocytes per flask for all three MOI spikes, both flasks tested were positive for infectivity by NDV. For the naïve donor, all flasks were positive at the 3000 cell level and all but the lowest MOI spike was positive at the 30 cell level. At the 3000 cell level for patient 521, 1 of 2 flasks were positive at the 0.02 MOI and 0 of 2 at the 0.002 MOI. At the 30 cell level for patient 521, 1 of 2 flasks were positive at the 0.2 MOI, all other flasks at this cell level were negative.

The plasma data show that in the naive patient, virus could be recovered from the plasma at all MOIs tested (see Table 3). However, no infectious virus was recovered from patient 521 plasma which contained neutralizing antibody.

Discussion: The results show that the number of leukocytes associated with infectious virus was reduced in patient 521 compared to the naïve donor. However, virus was still able to bind to leukocytes in the presence of neutralizing antibody. This binding was shown to occur even at low MOI (0.002), which is similar to the MOI for patient dosing.

NDV elicits a humoral immune response which results in the production of neutralizing antibody. Binding of virus to leukocytes may allow the virus to be protected from the neutralizing antibody. This is an advantage over free virus, which is exposed to the neutralizing antibody and rendered non-infectious.

It can be concluded from these data that using leukocytes as a vehicle to deliver virus to tumors is an advantage over free circulating virus which would be rendered non-infectious by neutralizing antibody in patients that have generated an immune response (ie. Patients which have received multiple doses of NDV).

TABLE 2

Evaluation of Leukocytes for the Presence of Bound Infectious NDV

| NDV Spike (MOI) | Number of Positive Cultures After Leukocytes are Placed in Co-Culture with a Monolayer of HT1080 Cells in a T25 Flask | | |
|---|---|---|---|
| | 300,000 Cells | 3000 Cells | 30 Cells |
| Naïve Donor | | | |
| 0.2 | 2* | 2 | 2 |
| 0.02 | 2 | 2 | 2 |
| 0.002 | 2 | 2 | 0 |
| No Spike (Ctl.) | 0 | 0 | 0 |
| Patient 521 | | | |
| 0.2 | 2* | 2 | 1 |
| 0.02 | 2 | 1 | 0 |
| 0.002 | 2 | 0 | 0 |
| No Spike (Ctl.) | 0 | 0 | 0 |

*Number of positive flasks per 2 flasks tested.

TABLE 3

Evaluation of Plasma for the Presence of Infectious NDV

| Sample | Naïve Donor | Patient 521 |
|---|---|---|
| 0.2 MOI Spike | 1 | 0 |
| 0.02 MOI Spike | 1 | 0 |
| 0.002 MOI Spike | 1 | 0 |
| No Spike (Control) | 0 | 0 |

N = 1 flask

As NDV is not pathogenic in man it is a surprising result to find that NDV binds preferentially to the white blood cell component of human blood.

Example 3

Preparation of Human Leukocyte/NDV Complex

Human Leukocytes ($5 \times 10^{+8}$ cells) are prepared by leukopheresis or by gradient centrifugation employing POLYMORPHPREP (Nycomed, Inc.) using the manufacturer's instructions. The cells are washed twice in sterile 1×PBS at room temperature and brought to a volume of 10 ml in the same buffer. The cells are mixed with $1 \times 10^{+10}$ pfu of NDV (added aseptically) and allowed to sit for 30 minutes (with further brief mixings at 10 and 20 minutes). The cells are centrifuged for 5 minutes at 1500 rpm and the PBS removed. The cells are washed with 20 ml of 1×PBS and centrifuged again. The cell pellet is diluted to 10 ml for injection.

Example 4

Treatment of Human Tumor Xenografts (<10 mm and >5 mm) in Athymic Mice with Human Leukocyte/NDV Complex Athymic mice are injected intradermally with 10 million human tumor cells. After tumors reached a size range of between 5 and 10 mm, a single injection of $8 \times 10^{+6}$ cells of the Leukocyte/NDV complex described in Example 3 is given. The effect of LVC on tumor growth is examined for complete and partial regressions.

Example 5

Systemic Treatment of Human Tumors with Human Leukocyte/NDV Complex in Patients

Human leukocytes are obtained by leukopheresis from patients. The leukocyte/NDV complex (LVC) is prepared as described in Example 3. The complex ($5 \times^{+8}$ cells) is returned to the patient by intravenous injection. Injections of LVC are given at three-day intervals for 21 days.

Example 6

Systemic Treatment of Human Tumors with Human Donor Leukocyte/NDV Complex in Patients Human leukocytes are obtained by leukopheresis from naïve donors. The leukocyte/NDV complex (LVC) is prepared as described in Example 3. The complex ($5 \times 10^{+8}$ cells) is returned to the patient by intravenous injection. Injections of LVC are given at three-day intervals for 21 days.

Example 7

Binding of NDV to Mouse Blood Cells

Purpose: Investigate the binding of NDV to mouse blood cells in order to determine which cell types bind the virus.

Materials: Reference lot RL-005 NDV; Antibody Mab2F12 (3.5 mg/ml) is raised to NDV HN protein; RD PharMingen Stain Buffer (PSB) containing 2% fetal bovine serum and 0.02% sodium azide, catalog #554656, lot M059394; Rockland goat anti-mouse polyclonal antibody—phycoerythrin conjugate, catalog #710-1832, lot 7367; Becton Dickinson Immunocytometry Systems 10×FACS Lysing Solution, Cat349202, lot#82026.

Method: Mouse whole blood was collected in citrate tubes (3.2%, 0.105M, Becton Dickinson #366415). Cells were counted using the trypan blue exclusion method and a hemocytometer. NDV lot number RL-005 (4.2E+10 PFU/ml) was used to infect the cells at MOIs (Multiplicity of Infection, expressed as PFU/cell) of 0.2, 1 and 3 (along with a negative control of no added virus). After virus was added, tubes were incubated at 37° C. for 30 minutes. Gentle mixing of the tubes to keep cells in suspension was performed at 3 intervals during the incubation period.

The samples were washed twice by adding 2 ml of cold PSB, centrifuging for 5 minutes, 4° C., 2000 rpm, and aspirating the solution away from the cell pellet. The PSB was removed each time by aspiration. The volumes of each sample were adjusted to 1 ml by adding cold PSB. The monoclonal antibody Mab2F12 was added to each sample by adding 20 ul of a solution containing 9.1 µg of the antibody. The samples were incubated for 30 minutes on ice and washed twice again as previously described. A goat anti-mouse—PE reporter antibody was added to each sample by adding 1 ml of a 12 μg/ml solution of this antibody. The samples were again incubated for 30 minutes on ice and washed as described. For analysis of the leukocyte fraction, 100 μl of each sample was incubated with 3 ml of 1×FACS Lysing Solution for 6 minutes at room temperature. The samples were centrifuged as before. The cell pellets were re-suspended in 0.5 ml of PSB. For erythrocyte analysis, 1.5 μl of each sample was added to 2.0 ml of PSB. Samples analysis was performed with a Becton Dickinson FACSCalibur flow cytometer. Forward and side scatter parameters employed linear settings and FL2 detection of phycoerythrin employed logarithmic settings.

Results: The results of the experiment shown in Table 4 indicate that unlike the binding of NDV to human blood cells where the virus preferentially binds to leukocytes (Example 1), NDV binds preferentially to the erythrocyte fraction of whole mouse blood and does not bind to the leukocytes.

TABLE 4

% Cells Positive for NDV Binding

| MOI | Erythrocytes | Leukocytes |
|---|---|---|
| 0.2 | 30 | 1 |
| 1 | 80 | 1 |
| 3 | 92 | 1 |

At an MOI of 0.2 where human leukocytes are mostly positive for the binding of NDV, mouse leukocytes are negative.

Example 8

Binding of NDV to Rat Blood Cells

Purpose: Investigate the binding of NDV to mouse Rat blood cells in order to determine which cell types bind the virus.

Materials: Reference lot RL-005 NDV; Antibody Mab2F12 (3.5 mg/ml) is raised to NDV HN protein; RD PharMingen Stain Buffer (PSB) containing 2% fetal bovine serum and 0.02% sodium azide, catalog #554656, lot M059394; Rockland goat anti-mouse polyclonal antibody—phycoerythrin conjugate, catalog #710-1832, lot 7367; Becton Dickinson Immunocytometry Systems 10×FACS Lysing Solution, Cat349202, lot#82026.

Method: Whole blood (1.8 ml) was collected in citrate tubes (3.2%, 0.105M, Becton Dickinson #366415) from a Sprague Dawley rat and kept at room temperature until use. Cells were counted using the trypan blue exclusion method and a hemocytometer. NDV lot number RL-005 (4.2E+10 PFU/ml) was used to infect the cells at MOIs (Multiplicity of Infection, expressed as PFU/cell) of 0.05, 0.2, 0.5, 1 and 3 (along with a negative control of no added virus). After virus was added, tubes were incubated at 37° C. for 30 minutes. Gentle mixing of the tubes to keep cells in suspension was performed at 3 intervals during the incubation period.

The samples were washed twice by adding 2 ml of cold PSB, centrifuging for 5 minutes, 4° C., 2000 rpm, and aspirating the solution away from the cell pellet. The PSB was removed each time by aspiration. The volumes of each sample were adjusted to 1 ml by adding cold PSB. The monoclonal antibody Mab2F12 was added to each sample by adding 20 ul of a solution containing 9.1 μg of the antibody. The samples were incubated for 30 minutes on ice and washed twice again as previously described. A goat anti-mouse—PE reporter antibody was added to each sample by adding 1 ml of a 12 μg/ml solution of this antibody. The samples were again incubated for 30 minutes on ice and washed as described. For analysis of the leukocyte fraction, 100 μl of each sample was incubated with 3 ml of 1×FACS Lysing Solution for 6 minutes at room temperature. The samples were centrifuged as before. The cell pellets were re-suspended in 0.5 ml of PSB. For erythrocyte analysis, 1.5 μl of each sample was added to 2.0 ml of PSB. Samples analysis was performed with a Becton Dickinson FACSCalibur flow cytometer. Forward and side scatter parameters employed linear settings and FL2 detection of phycoerythrin employed logarithmic settings.

Results: The results of the experiment shown in Table 5 indicate that NDV binds to rat leukocytes at a low MOI (0.02 and 0.05) while it does not bind well to the erythrocytes at these MOI's. The pattern appears to be intermediate between the binding of the virus to human leukocytes to which it binds preferentially and to mouse leukocytes, to which it does not bind.

TABLE 5

| | % Cells Positive for NDV Binding | |
|---|---|---|
| MOI | Erythrocytes | Leukocytes |
| 0.02 | 3 | 7 |
| 0.05 | 12 | 21 |
| 0.2 | 30 | 29 |
| 1 | 63 | 58 |
| 3 | 90 | 66 |

Example 9

Binding of NDV to Human Platelets

Purpose: Investigate the binding of NDV to human platelets

Materials: Reference lot RL-005 NDV; Antibody Mab2F12 (3.5 mg/ml) is raised to NDV HN protein; BD PharMingen Stain Buffer (PSB) containing 2% fetal bovine serum and 0.02% sodium azide, catalog #554656, lot M059394; Rockland goat anti-mouse polyclonal antibody—phycoerythrin conjugate, catalog #710-1832, lot 7367; Becton Dickinson Immunocytometry Systems 10×FACS Lysing Solution, Cat349202, lot#82026.

Method:

Isolation of Platelets

Whole human blood was collected in citrate tubes (3.2% 0.105M Citrate, Becton Dickinson #366415). Seven milliliters of whole blood were placed into a 15 ml polypropylene centrifuge tube. The tube was centrifuged at 800 g for 5 minutes at room temperature. Approximately 1.5 ml of platelet-rich plasma (PRP) was collected from the top of the centrifuge tube. Based on published values for yield, the sample was determined to contain 8.0E+8 cells/ml. 100% of PRP was infected with NDV (RL-005) at MOIs of 0.1, 10 and 100 for 30 minutes at room temperature.

The samples were washed twice by adding 2 ml of cold PSB, centrifuging for 5 minutes, 4° C., 2000 rpm, and aspirating the solution away from the cell pellet. The PSB was removed each time by aspiration. The volumes of each sample were adjusted to 1 ml by adding cold PSB. The monoclonal antibody Mab2F12 was added to each sample by adding 20 ul of a solution containing 9.1 μg of the antibody. The samples were incubated for 30 minutes on ice and washed twice again as previously described. A goat anti-mouse—PE reporter antibody was added to each sample by adding 0.1 ml of a 12 µg/ml solution of this antibody. The samples were again incubated for 30 minutes on ice and washed as described. Sample analysis was performed with a Becton Dickinson FACSCalibur flow cytometer. Forward and side scatter parameters employed linear settings and FL2 detection of phycoerythrin employed logarithmic settings.

Results: The results of the experiment shown in Table 6 indicate that NDV binds to human platelets. The number of platelets that are positive for binding of NDV does not increase greatly in the MOI range tested although the mean fluorescence does, indicating that more NDV binds to the positive portion of the platelets as the MOI increases.

TABLE 6

NDV Binding To Human Platelets

| MOI | % Positive Platelets | Mean Fluorescence |
|---|---|---|
| 0 | 0 | 10 |
| 1 | 67 | 258 |
| 10 | 81 | 616 |
| 100 | 73 | 1005 |

Example 10

Binding Hierarchy of NDV to Human Leukocytes

Materials: Reference lot RL-005 NDV; Antibody Mab2F12 (3.5 mg/ml) was raised to NDV HN protein; BD PharmMingen™ Stain Buffer (PSB) containing 2% fetal bovine serum and 0.02% sodium azide, catalog #544656, lot M059394; Rockland goat anti-mouse polyclonal antibody-phycoerythrin conjugate, catalog #710-1832, lot 7367; Becton Dickinson Immumocytometry Systems™ 10×FACS Lysing Solution Cat. 349202, Lot#82026.

Method: Human whole blood was collected in citrate tubes (3.2%, 0.105M, Becton Dickinson™ #366415). Approximately 4 ml from each of two tubes was pooled and kept at room temperature until use. Cells were counted using the trypan blue exclusion method and a hemocytometer. NDV lot number RL-004 (1.3E+10 PFU/ml) was used to infect 100 μl samples of whole blood at MOIs (Multiplicity of Infection, expressed as PFU/cell) of 0, 0.005, 0.01, 0.02, 0.05, 0.1, and 0.2 to the whole blood. After virus was added, samples were incubated at 37° C. for 30 minutes.

The samples were washed twice by adding 2 ml of cold PSB, centrifuging for 5 minutes, 4° C., 2000 rpm, and aspirating the solution away from the pellet. The volumes of each sample were adjusted to 100 μl with PSB. Monoclonal antibody Mab2F12 was added to each sample by adding 2 μl of a solution made in PSB containing 1 μg of the antibody. The samples were incubated for 30 minutes on ice and washed twice again as previously described. The goat anti-mouse—PE reporter antibody was added to each sample by adding 100 μl of a 12 μg/ml solution of this antibody diluted 2.4:1 in PSB. The samples were incubated for 30 minutes on ice and washed as described above. To prepare the samples for leukocyte cell analysis, each sample was incubated with 3 ml of 1×FACS Lysing Solution for 6 minutes at room temperature, then centrifuged and aspirated as before. The cell pellets were re-suspended in 0.5 ml of PSB. Sample analysis was performed with a Becton Dickinson FACS-Calibur™ flow cytometer. Granulocyte, lymphocyte and monocyte populations were gated by comparing the forward scatter and side scatter parameters for each sample. This was used to determine the number of cells positive for binding the virus and the mean fluorescence value of each of these populations for each sample.

The results (Table 7) indicate that NDV binds preferentially to the three cell populations. The order of preference is: monocyte>granulocyte>>lymphocyte. Furthermore, as shown from the mean fluorescence data, the monocyte population binds substantially more NDV than does the granulocyte population, and binds much more virus than does the lymphocyte cell population.

TABLE 7

| | % Positive Cells | | | Mean Fluorescence | | |
|---|---|---|---|---|---|---|
| MOI | Monocyte | Granulocyte | Lymphocyte | Monocyte | Granulocyte | Lymphocyte |
| 0 | 2 | 2 | 2 | 13 | 19 | 7 |
| 0.005 | 80 | 68 | 19 | 65 | 20 | 9 |
| 0.01 | 92 | 97 | 39 | 134 | 35 | 11 |
| 0.02 | 99 | 100 | 54 | 219 | 66 | 16 |
| 0.05 | 98 | 100 | 72 | 314 | 113 | 22 |
| 0.10 | 99 | 100 | 84 | 448 | 154 | 31 |
| 0.20 | 100 | 100 | 96 | 692 | 251 | 69 |

What is claimed is:

1. A method of treating a human subject with cancer, comprising administering to the subject an amount of a pharmaceutical composition effective to treat the subject, the pharmaceutical composition comprising human leukocytes and a replication-competent oncolytic virus in suspension in a physiologically acceptable solution, wherein the virus binds specifically to the leukocytes; and the ratio of plaque-forming units of the virus to number of leukocytes in the composition is at least 1:100, thereby treating the subject:

wherein the leukocytes comprise an immortalized cell line.

2. The method of claim 1, wherein the immortalized cell line is U-937 or KG-1.

3. A method of treating a human subject with cancer, comprising administering to the subject an amount of a pharmaceutical composition effective to treat the subject, the pharmaceutical composition comprising human leukocytes and a replication-competent oncolytic virus in suspension in a physiologically acceptable solution, wherein the virus binds specifically to the leukocytes, and
the ratio of plaque-forming units of the virus to number of leukocytes in the composition is at least 1:100,
thereby treating the subject;
wherein the pharmaceutical composition comprises the oncolytic virus suspended in whole blood.

4. A method of treating a human subject with cancer, comprising
administering to the subject an amount of a pharmaceutical composition effective to treat the subject, the pharmaceutical composition comprising human leukocytes and a replication-competent oncolytic virus in suspension in a physiologically acceptable solution, wherein
the virus binds specifically to the leukocytes; and
the ratio of plaque-forming units of the virus to number of leukocytes in the composition is at least 1:100,
thereby treating the subject;
wherein the composition is administered intravesicularly.

5. The method of claim 4, wherein the volume of composition administered is up to seventy-five milliliters.

6. The method of claim 5, wherein the volume of composition administered is from fifty to sixty milliliters.

7. A method of treating a human subject with cancer, comprising
administering to the subject an amount of a pharmaceutical composition effective to treat the subject, the pharmaceutical composition comprising human cells infected with an oncolytic virus in suspension in a physiologically acceptable solution,
wherein the cells are leukocytes or platelets, thereby treating the subject;
wherein the cells comprise an immortalized cell line.

8. The method of claim 7, wherein the immortalized cell line is U-937 or KG-1.

9. A method of treating a human subject with cancer, comprising administering to the subject an amount of a pharmaceutical composition effective to treat the subject, the pharmaceutical composition comprising human cells infected with an oncolytic virus in suspension in a physiologically acceptable solution, wherein the cells are platelets, thereby treating the subject.

10. A method or treating a human subject with cancer, comprising
administering to the subject an amount of a pharmaceutical composition effective to treat the subject, the pharmaceutical composition comprising human cells infected with an oncolytic virus in suspension in a physiologically acceptable solution,
wherein the cells are leukocytes or platelets, thereby treating the subject;
wherein the infected cells are at least one-tenth of one percent of the total number of leukocytes and platelets in the composition.

11. The method of claim 10, wherein the infected cells are at least thirty percent of the total number of leukocytes and platelets in the composition.

12. A method of treating a human subject with cancer, comprising administering to the subject an amount of a pharmaceutical composition effective to treat the subject, the pharmaceutical composition comprising human cells infected with an oncolytic virus in suspension in a physiologically acceptable solution, wherein the cells are platelets, thereby treating the subject; wherein the effective amount is a daily dosage containing from $10^9$ to $10^{11}$ platelets per square meter of patient surface area.

13. The method of claim 12, wherein the daily dosage contains about $10^{11}$ platelets per square meter of patient surface area.

14. The method of claim 12, wherein the daily dosage is administered in a single administration.

15. The method of claim 12, wherein the daily dosage is administered at a frequency of from one to seven times in a one-week period.

* * * * *

UNITED STATES PATENT AND TRADEMARK OFFICE
CERTIFICATE OF CORRECTION

PATENT NO. : 7,122,182 B2
APPLICATION NO. : 10/142405
DATED : October 17, 2006
INVENTOR(S) : William S. Groene It is certified that error appears in the above-identified patent and that said Letters Patent is hereby corrected as shown below:

On the Title page, Item (75), delete "Stephen N. Mueller, Myersville, MA (US)".

Signed and Sealed this

Second Day of January, 2007

JON W. DUDAS
*Director of the United States Patent and Trademark Office*